(12) United States Patent
Jörneus et al.

(10) Patent No.: US 9,259,299 B2
(45) Date of Patent: Feb. 16, 2016

(54) COMPONENTS FOR THREADING OF BONE

(75) Inventors: Lars Jörneus, Frillesås (SE); Henrik Petersson, Zürich (CH)

(73) Assignee: Nobel Biocare Services AG, Kloten (CH)

( * ) Notice: Subject to any disclaimer, the term of this patent is extended or adjusted under 35 U.S.C. 154(b) by 20 days.

(21) Appl. No.: 13/394,532

(22) PCT Filed: Sep. 6, 2010

(86) PCT No.: PCT/EP2010/005449
§ 371 (c)(1),
(2), (4) Date: Apr. 12, 2012

(87) PCT Pub. No.: WO2011/026644
PCT Pub. Date: Mar. 10, 2011

(65) Prior Publication Data
US 2012/0191097 A1    Jul. 26, 2012

(30) Foreign Application Priority Data
Sep. 7, 2009  (EP) .................................... 09011435

(51) Int. Cl.
*A61B 8/00* (2006.01)
*A61B 17/16* (2006.01)
(Continued)

(52) U.S. Cl.
CPC ........... *A61C 8/0089* (2013.01); *A61B 17/1655* (2013.01); *A61C 1/084* (2013.01)

(58) Field of Classification Search
CPC ........................ A61C 8/0089; A61B 17/1655
USPC ........................................................ 81/436
See application file for complete search history.

(56) References Cited

U.S. PATENT DOCUMENTS 5,364,400 A * 11/1994 Rego, Jr. ............ A61B 17/8645
  606/304
5,489,307 A  2/1996 Kuslich et al.
5,593,410 A  1/1997 Vrespa
(Continued)

FOREIGN PATENT DOCUMENTS

DE  27 44 564    4/1979
EP  1 759 658    3/2007
(Continued)

OTHER PUBLICATIONS

International Search Report for Application No. PCT/EP2010/005448 (the PCT counterpart of U.S. Appl. No. 13/394,524) mailed on Dec. 21, 2010 in 4 pages.
(Continued)

*Primary Examiner* — David Bates
(74) *Attorney, Agent, or Firm* — Knobbe, Martens, Olson & Bear LLP

(57) ABSTRACT

In certain embodiments, a combination of a thread forming tool and an implant is disclosed. The thread forming tool can have a thread forming section with a helical thread having at least one cutting surface for cutting a thread in bone. The implant can include a bone apposition surface having at least one helical thread for position at least partially in the thread of the bone. A longitudinal cross-sectional shape of at least a portion of the helical thread of the thread forming section in certain embodiments, substantially corresponds to a longitudinal cross-sectional shape of at least a portion of the helical thread of the implant.

13 Claims, 9 Drawing Sheets

(51) Int. Cl.
*A61C 8/00* (2006.01)
*A61C 1/08* (2006.01)

(56) References Cited

U.S. PATENT DOCUMENTS

| | | | |
|---|---|---|---|
| 5,643,269 A * | 7/1997 | Harle | 606/79 |
| 5,741,267 A | 4/1998 | Jorneus et al. | |
| 6,086,595 A | 7/2000 | Yonemura et al. | |
| 6,120,506 A | 9/2000 | Kohrs et al. | |
| 6,196,842 B1 | 3/2001 | Jorneus | |
| 6,283,966 B1 | 9/2001 | Houfburg | |
| 6,863,529 B2 | 3/2005 | Strong et al. | |
| 6,896,517 B1 | 5/2005 | Bjorn et al. | |
| 7,008,228 B2 | 3/2006 | Bjorn et al. | |
| 7,175,435 B2 | 2/2007 | Andersson et al. | |
| 7,247,020 B2 | 7/2007 | Takahashi et al. | |
| 7,572,125 B2 | 8/2009 | Brajnovic | |
| 7,621,916 B2 * | 11/2009 | Lauryssen et al. | 606/86 R |
| 7,845,946 B2 | 12/2010 | Brajnovic | |
| 7,950,924 B2 | 5/2011 | Brajnovic | |
| 8,142,189 B2 | 3/2012 | Brajnovic | |
| 8,157,563 B2 | 4/2012 | Brajnovic | |
| 8,186,999 B2 | 5/2012 | Andersson et al. | |
| 8,740,912 B2 | 6/2014 | Stark | |
| 2002/0022862 A1 * | 2/2002 | Grafton | A61B 17/0401 606/232 |
| 2002/0116006 A1 | 8/2002 | Cohen | |
| 2002/0138079 A1 | 9/2002 | Cohen | |
| 2004/0260291 A1 * | 12/2004 | Jensen | 606/69 |
| 2005/0026114 A1 | 2/2005 | Nilo et al. | |
| 2006/0008763 A1 | 1/2006 | Brajnovic | |
| 2006/0008770 A1 | 1/2006 | Brajnovic et al. | |
| 2006/0079894 A1 * | 4/2006 | Colleran et al. | 606/61 |
| 2007/0093837 A1 * | 4/2007 | Bohrmann et al. | 606/69 |
| 2007/0099153 A1 | 5/2007 | Fromovich | |
| 2007/0293867 A1 | 12/2007 | Anitua | |
| 2008/0038692 A1 | 2/2008 | Andersson et al. | |
| 2008/0118895 A1 | 5/2008 | Brajnovic | |
| 2008/0153065 A1 | 6/2008 | Brajnovic et al. | |
| 2008/0261175 A1 | 10/2008 | Hurson | |
| 2009/0136898 A1 * | 5/2009 | Kim | A61B 17/1655 433/165 |
| 2009/0138053 A1 * | 5/2009 | Assell | A61F 2/4405 606/301 |
| 2009/0239197 A1 | 9/2009 | Brajnovic | |
| 2009/0253097 A1 | 10/2009 | Brajnovic | |
| 2010/0009314 A1 | 1/2010 | Tardieu et al. | |
| 2010/0062389 A1 | 3/2010 | Drews et al. | |
| 2011/0008751 A1 | 1/2011 | Pettersson | |
| 2012/0123576 A1 | 5/2012 | Pettersson et al. | |
| 2012/0191103 A1 | 7/2012 | Jorneus et al. | |

FOREIGN PATENT DOCUMENTS

| | | |
|---|---|---|
| FR | 2 735 008 | 12/1996 |
| WO | WO 2004/103202 | 12/2004 |
| WO | WO 2005/011514 | 2/2005 |
| WO | WO 2006/014130 | 2/2006 |
| WO | WO 2008/128757 | 10/2008 |
| WO | WO 2011/026643 | 3/2011 |

OTHER PUBLICATIONS

International Preliminary Report on Patentability for Application No. PCT/EP2010/005448 (the PCT counterpart of U.S. Appl. No. 13/394,524) issued Mar. 13, 2012 in 8 pages.

International Search Report for Application No. PCT/EP2010/005449 (the PCT counterpart of this application) mailed on Mar. 23, 2011 in 6 pages.

International Preliminary Report on Patentability for Application No. PCT/EP2010/005449 (the PCT counterpart of this application) issued Mar. 13, 2012 in 8 pages.

Dentsply Friadent: "XiVE—ExpertEase Chirurgie Step-by-Step", Mar. 19, 2009 (cited on International Search Report for PCT/EP2010/005449; 6 pages retrieved from http://www.dentsply-friadent.com/downloads on Feb. 14, 2012).

* cited by examiner

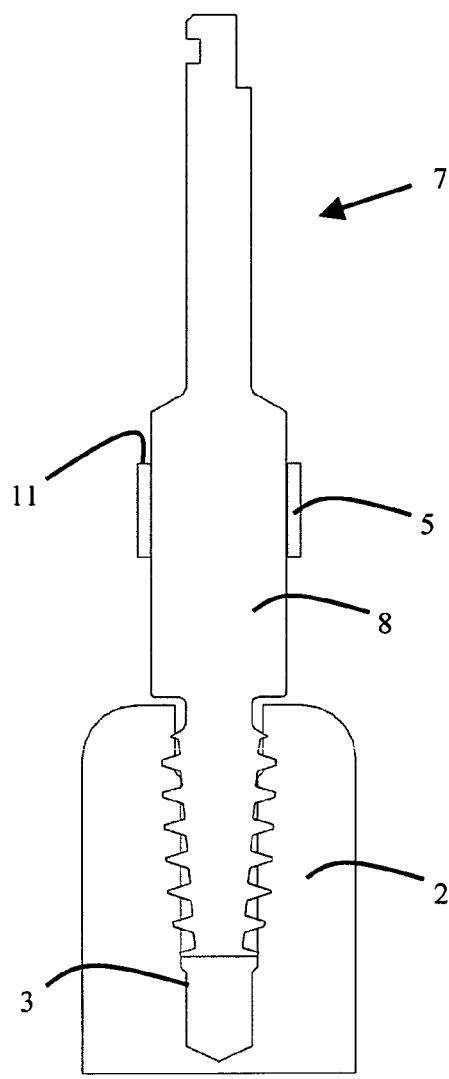
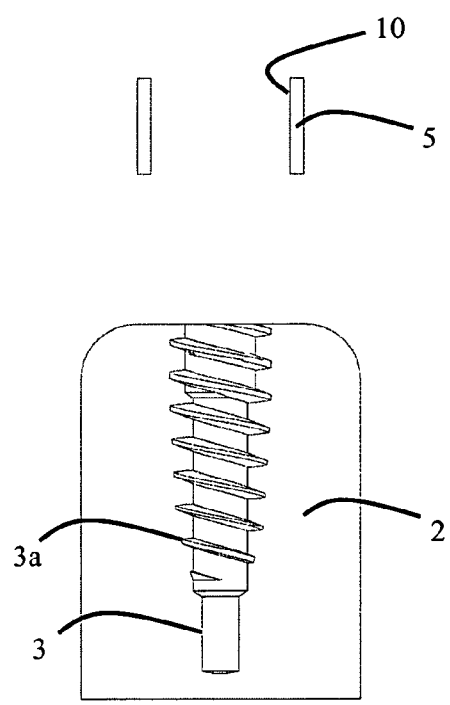
Fig. 1c
Fig. 1d

COMPONENTS FOR THREADING OF BONE

CROSS-REFERENCE TO RELATED APPLICATIONS

This application is a national stage application under 35 U.S.C. §371 of PCT Application No. PCT/EP2010/005449, filed on Sep. 6, 2010, which published in English as WO 2011/026644 A1 on Mar. 10, 2011 and which claims priority benefit of European Patent Application No. 09011435.6, filed on Sep. 7, 2009, the entire contents of which applications and publication are herein incorporated by reference in their entirety.

BACKGROUND

1. Field of the Invention

This invention pertains in general to the field of implant surgery. More particularly, the invention relates to a combination of a thread forming tool and an implant. The components may be used separately or in a system for drill and implant guided surgery.

2. Description of the Related Art

In certain clinical applications when the implant is placed, such as placement in a jawbone, the implant has a tendency to deviate from its anticipated trajectory, for example due to varying density of the bone surrounding the implant, both in the vertical as well as the lateral direction of the implant. If, for example, the bone is denser one side of the central longitudinal axis of the implant, it will often deviate towards the softer bone, and end up in a non-optimal position, which is different from a planned position. If this happens during guided surgery, the implant mount, which is guided by a guide sleeve of the surgical template, may jam in the guide sleeve.

Furthermore, most implant types are wider at the coronal end than at the apical end. The increase in width from the apical to the coronal end can be of two types, a) a substantially cylindrical implant with a wider coronal platform, or b) a tapered implant tapering from its apical end at least partially towards its coronal end. Such tapered implants sometimes tend to deviate from the anticipated path of trajectory. This is especially true for so called bone-condensing implants (type b above), wherein the diameter of the implants may be gradually larger than the recess formed in the bone. For such bone/condensing implants, it is desired to have relatively uniform condensation of the bone at a specific lateral cross section of the implant. Of course, the level of condensation also depends on the quality of the bone, i.e. whether it is softer or harder bone quality, which may differ along the length of the implant when placed.

Hence, an improved combination of components for placement of an implant would be advantageous and in particular allowing for improved precision, increased flexibility, cost-effectiveness, and/or patient safety would be advantageous.

SUMMARY

Accordingly, certain embodiments of the present disclosure preferably seek to mitigate, alleviate or eliminate one or more deficiencies, disadvantages or issues in the art, such as the above-identified, singly or in any combination by providing combination of components for placement of an implant according to the appended patent claims.

According to a first aspect of certain embodiments, a combination comprises a thread forming tool and an implant. For example, in certain embodiments, the thread forming tool has a thread forming section with a helical thread having at least one cutting surface for cutting a thread in bone. The implant of certain embodiments comprises a bone apposition surface having at least one helical thread for position at least partially in the thread of the bone. A longitudinal cross-sectional shape of at least a portion of the helical thread of the thread forming section substantially corresponds to a longitudinal cross-sectional shape of at least a portion of the helical thread of the implant in certain embodiments.

A dimension of said cross-sectional shape of the helical thread of the thread forming section may substantially correspond to a corresponding dimension of said cross-sectional shape of the helical thread of the implant.

A dimension of said cross-sectional shape of the helical thread of the thread forming section may be smaller than a corresponding dimension of said cross-sectional shape of the helical thread of the implant.

The dimension of the thread forming section may be the radius from the central longitudinal axis of the thread forming tool to an external surface of a tip of its thread. The dimension of the thread of the implant may be the radius from the central longitudinal axis of the implant to an external surface of a tip of its thread.

The dimension of the thread forming section may be the radius from the central longitudinal axis of the thread forming tool to an external surface of a root of its thread. The dimension of the thread of the implant may be the radius from the central longitudinal axis of the implant to an external surface of a root of its thread.

A pitch of the helical thread of the thread forming section may be substantially equal to a pitch of the helical thread of the implant.

The thread forming section may be at least partially tapering outwardly from its apical end towards its coronal end. An apical portion of the implant may be least partially tapering outwardly from its apical end towards its coronal end.

A maximum diameter of at least an apical portion of the bone tissue apposition surface may be smaller than or equal to a maximum diameter of the thread forming section of the thread forming tool.

A maximum diameter of an apical portion of the bone apposition surface may be larger than a maximum diameter of an apical portion of the thread forming section of the thread forming tool, and smaller than a coronal portion of the thread forming section of the thread forming tool.

A maximum diameter of a coronal portion of the bone tissue apposition surface may be larger than a maximum diameter of a coronal portion of the thread forming section of the thread forming tool.

The combination may further comprise a drill, and a guide sleeve for a surgical template. The guide sleeve may have a guide surface for guiding the thread forming tool. The drill may have at least one cutting edge on the apical section and the coronal section. The thread forming tool may have a guide section for guidance by the guide surface of the guide sleeve. Also, the thread forming section may comprise an apical portion, and a coronal portion. A maximum diameter of the apical portion of the thread forming section may be smaller than or equal to a maximum diameter of the cutting edge of the drill.

A position of the maximum diameter of the apical portion of the thread forming section may be located offset from an apical end of the thread forming section. The position may also be located at a first distance from an apical end of the guide section. The first distance may be substantially equal to a second distance from said position to a coronal end of the guide surface when the thread forming tool is inserted into the guide sleeve.

The offset may be at least 1 mm, preferably at least 2 mm, for example in the range of 2-3 mm.

An apical end of the thread forming section may be larger than a maximum diameter of an apical section of the drill, which is smaller than a maximum diameter of a coronal section of the drill.

According to a second aspect of certain embodiments, a method of placing an implant in a threaded recess in bone, comprises drilling a recess in bone, forming a thread in the recess having a shape which at least partially corresponds to a shape of a thread of an implant, and inserting said implant in said threaded recess.

Further embodiments are defined in the dependent claims, wherein features for the second aspect of certain embodiments are as for the first aspect mutatis mutandis.

Some embodiments of the disclosure provide for improved accuracy of a position of an implant in bone. Furthermore, some embodiments of the disclosure provide for a relatively uniform distribution of load from the implant to the bone when the implant is placed. Hence, this provides for placement of the implant in an anticipated trajectory, i.e. the implant does not deviate from the anticipated trajectory. Hence, the implant may be more accurately centered within a recess of the bone, whereby more uniformly condensing of the bone around the periphery of the threads of the implant is provided for. Some embodiments of the disclosure provide for reducing or eliminating one or several of an angular, a vertical, a centering, and/or a lateral deviation compared to an anticipated and/or planned position of the implant. Some embodiments of the disclosure also provide for using bone-condensing implants, such as implants tapering outwards from its apical end towards its coronal end, in guided implant surgery and/or in hard bone applications.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which certain embodiments of the disclosure are capable of will be apparent and elucidated from the following description of certain embodiments of the present disclosure, reference being made to the accompanying drawings, in which FIGS. 1a-1d are cross-sectional views of certain embodiments of a thread forming tool, a guide sleeve, and a recess formed in bone using a drill;

DETAILED DESCRIPTION

Figure 1A:
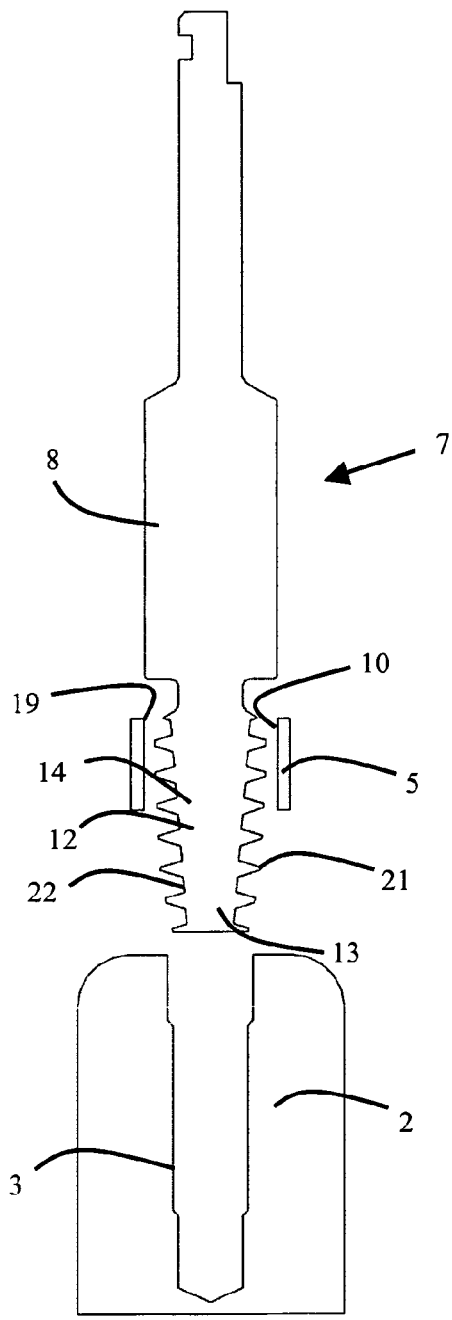

Specific embodiments will now be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on certain embodiments of the present disclosure applicable to installing a dental implant in the jawbone. However, it will be appreciated that the invention is not limited to this application but may be applied to many other procedures, such as oral and cranio-maxillofacial implant placement in anywhere in bone in the cranium etc. Certain embodiments of the disclosure may be used separately or as port of a drill and implant guided planning and treatment concept.

Components according to some embodiments provide for passively inserting an implant in bone at least initially when it is placed. Passively threading means in the context of certain embodiments that the implant can be inserted, such as by hand, to a certain depth without condensing the bone. The implant may contact the bone, but substantially not condense. Hence, a passive fit between the implant and the bone is provided. This provides for the implant more closely following an anticipated trajectory. Additionally or alternatively, a more uniform compression of bone when the implant is placed may be obtained, which in it self may contribute to that the implant follows the anticipated trajectory.

Figure 5A:
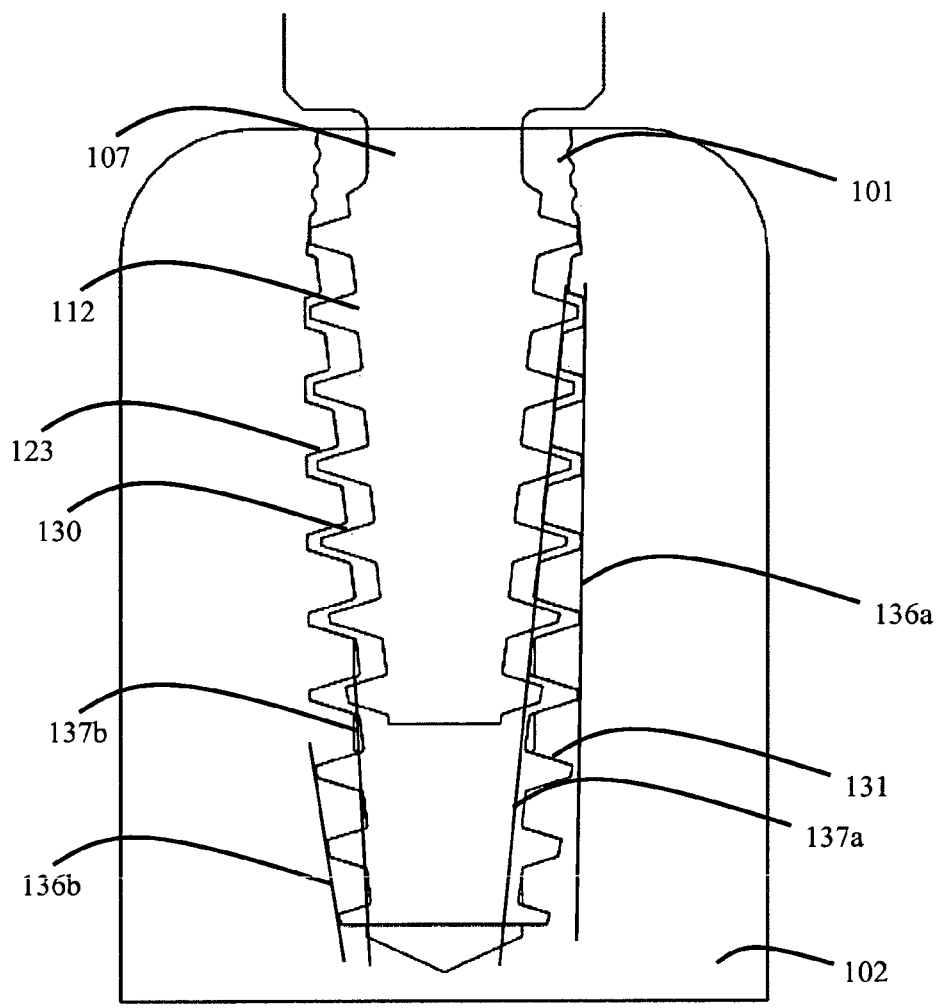
FIGS. 5a-5c overlaid cross-sectional views of certain embodiments of the implant and the thread forming tool.
Figure 5B:
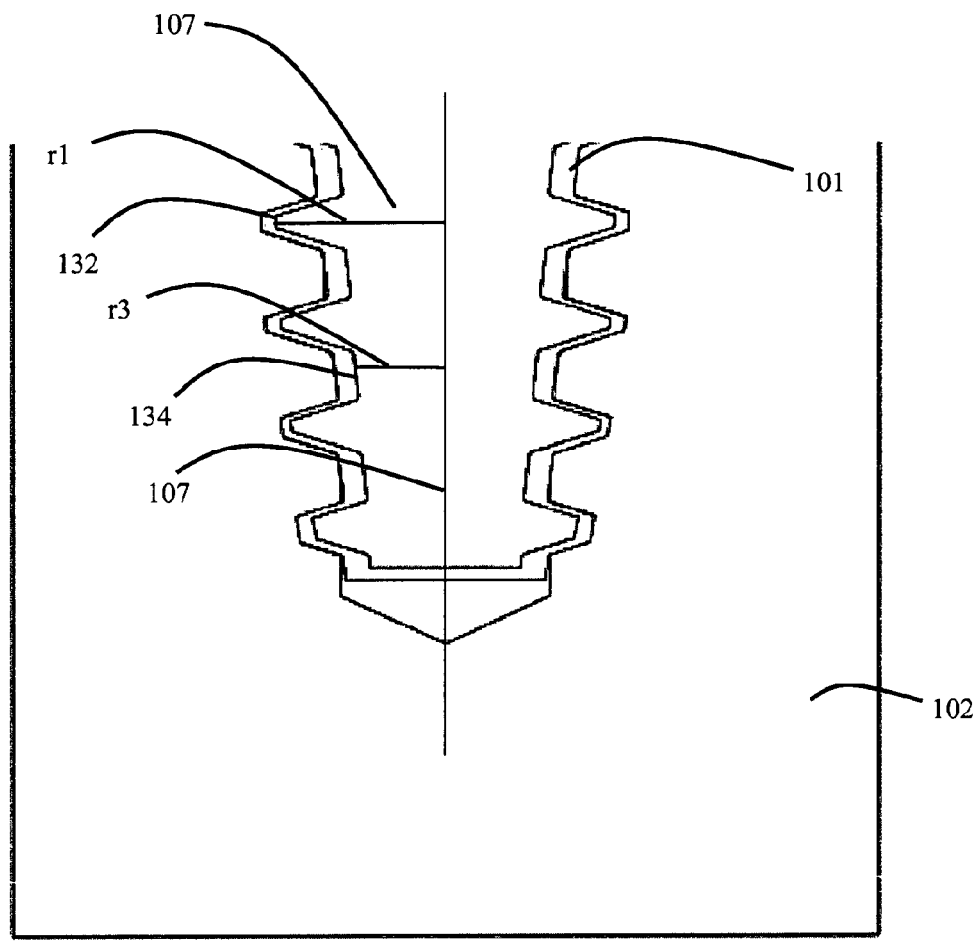
Figure 5C:
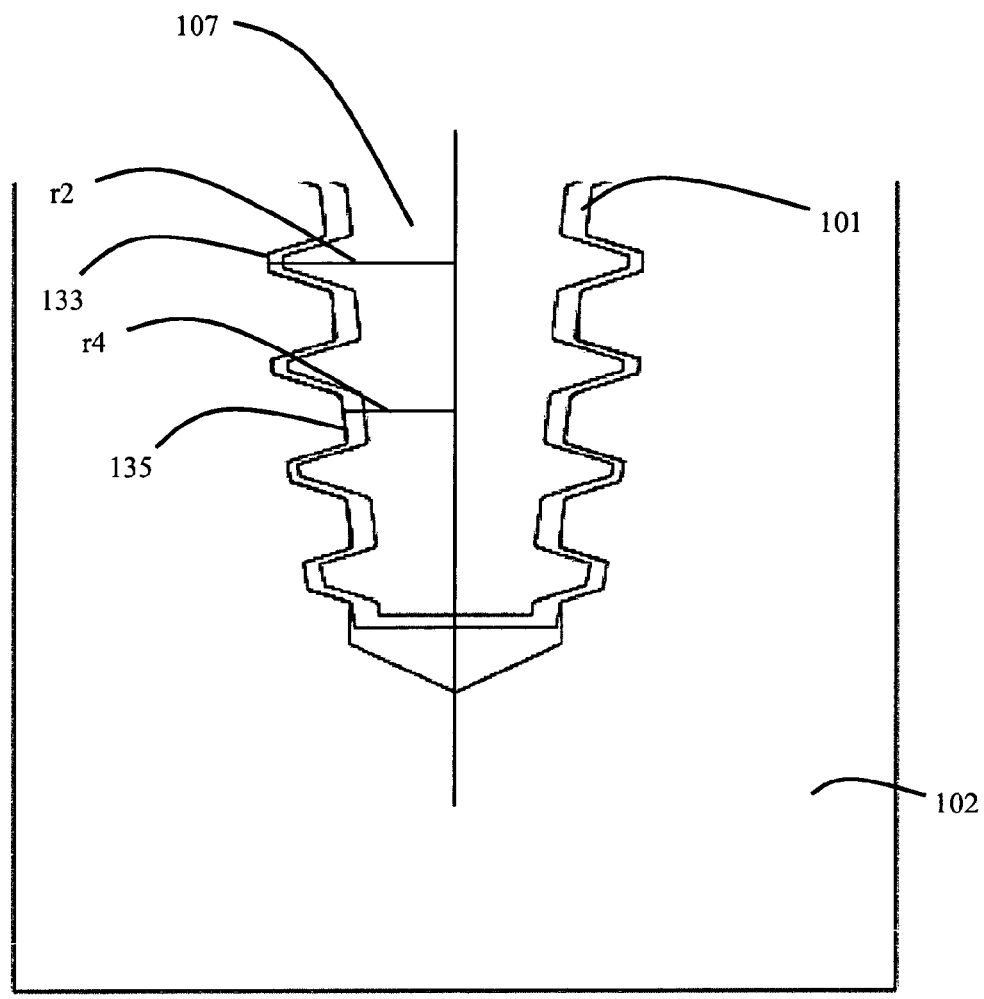

FIG. 5a-5c illustrates some embodiments, wherein longitudinal cross/sectional views of an implant 101 and a thread forming tool 107 are overlaid. The thread forming tool 107 comprises a thread forming section 112 with a helical thread 130 having at least one cutting surface for cutting a thread in bone 102. The implant 101 comprises a bone apposition surface 123 having at least one helical thread 131 for position at least partially in a thread of the bone 102. In certain embodiments, a longitudinal cross-sectional shape of at least a portion of the helical thread 130 of the thread forming section substantially corresponds to a longitudinal cross-sectional shape of at least a portion of the helical thread 131 of the implant 101. This provides for substantially uniform distribution of load from the implant 101 to the bone 103 when the implant is inserted. This may, in turn, additionally provide for a more predictable path of trajectory when the implant 101 is placed in the bone 102.

The longitudinal cross-sectional shape of the helical thread 130, 131 of the thread forming section 112 and the implant, respectively, may comprise the thread profile including the root of the thread, the tip of the thread, and the thread flank extending between the root of the thread to the tip of the thread. In the illustrated embodiment, the tip of the threads 130, 131 comprises a flat face. The flat face may vary in width in the axial direction of the thread 130, 131. Furthermore, the root of the thread 130, 131 may form a substantially flat surface having a width. The shape of the root of the thread may be constant in the axial direction of the thread. Each of the tip, root, and/or flank of the thread may comprise at least one recess in the micrometer range for promotion of osseointegration.

In some embodiments, a dimension of the cross-sectional shape of the helical thread 130 of the thread forming section 112 substantially corresponds to a corresponding dimension of the cross-sectional shape of the helical thread 131 of the implant 101. In other embodiments, the dimension of the cross-sectional shape of the helical thread 130 of the thread forming section 120 is smaller than a corresponding dimension of the cross-sectional shape of the helical thread 131 of the implant 101. The smaller the dimension is, the more condensing of the bone may be provided for. Hence, for applications in harder bone the difference of the dimensions may be smaller than for applications in softer bone.

For example, in certain embodiments, the dimension of the thread forming section 112 and the implant 101 are measured when they are aligned in a position which is their optimal final position, such as is illustrated in FIGS. 5a-5c. The dimension may then be measured at a lateral cross section of the threaded section 112 and the implant 101 which is located at the same distance from the coronal end of the implant 101. Hence, in certain embodiments, the dimensions are measured when the threaded section 112 is vertically aligned with the implant 101 and the threads 130, 131 are rotationally aligned, i.e. the threads uniformly overlap. In some embodiments, the dimension of the thread forming section 112 is a radius r1 (FIG. 5b) from the central longitudinal axis of the thread forming tool 112 to an external surface of a tip 132 of the thread 130 of the thread forming section 112. The corresponding dimension of the thread 131 of the implant 101 is a radius r2 (FIG. 5c) from the central longitudinal axis of the implant to an external surface of a tip 133 of its thread 131 for a lateral cross section taken at the same distance, as for measuring r1, from the coronal end of the implant 101.

Alternatively or additionally, the dimension of the thread forming section 112 is a radius r3 (FIG. 5b) from the central longitudinal axis of the thread forming tool 112 to an external surface of a root 134 of its thread. A corresponding dimension of the thread 131 of the implant 101 is a radius r4 (FIG. 5c) from the central longitudinal axis of the implant 101 to an external surface of a root 135 of its thread. In some embodiments, the dimensions for the root are measured in the same way as for the dimension for the tips 132, 133, as described above.

In some embodiments, a pitch of the helical thread 130 of the thread forming section 112 is substantially equal to a pitch of the helical thread 131 of the implant 101. The pitch is the distance from the crest of the thread to the next crest when the thread is viewed in longitudinal cross section. In some embodiments of the disclosure, the threads 130, 131 of the threaded section 112 and the implant 101, respectively, may be single or multiple lead threads.

In the embodiment of FIG. 5a, the thread forming section 112 is at least partially tapering outwardly from its apical end towards its coronal end. Similarly, an apical portion, such as the entire or a portion of the threaded section of the implant 101, of the implant 101 is least partially tapering outwardly from its apical end towards its coronal end. For example, either or both of the tip 133 and the root 135 of the thread 131 of the implant taper relative the central longitudinal axis of the implant 101. Alternatively, at least a portion of the tip 133 is substantially cylindrical and at least a portion of the root 135 of the thread 131 in the axial direction of the helical thread of the implant 101 taper relative the central longitudinal axis of the implant 101. In FIG. 5a, the level of taper of the tip or crest 133 of the thread 131 has been indicated by straight lines 136a, 136b interconnecting a number of tip sections along various portions of the thread along the longitudinal axis of the implant 101. Also, the level of taper of the root 135 of the thread 131 has been indicated by straight lines 137a, 137b interconnecting a number of root sections along various portions of the thread 131 along the longitudinal axis of the implant 101. As can be seen in this example, the level of taper at the coronal end of the implant 101 compared to the apical end of the implant is less for both the tip 133 and root 135. Each root section may also taper more than the general taper of a number of subsequent root sections. This is described for improved bone-condensing properties, which is described in more detail in WO2004103202 and WO2008128757, which are incorporated herein by reference in their entirety for all purposes. The thread 131 of the thread forming section 112 may have the same general taper as the thread 131 of the implant 101.

In some embodiments, a maximum diameter of at least an apical portion of the bone tissue apposition surface 123 is smaller than or equal to a maximum diameter of the thread forming section 112 of the thread forming tool 107. This provides for passively threading the implant at least to a certain extent before condensing of the bone commences. The passively threading may correspond to the offset O discussed below.

In some embodiments, a maximum diameter of an apical portion of the bone apposition surface 123 is larger than a maximum diameter of an apical portion of the thread forming section of the thread forming tool, and smaller than a coronal portion of the thread forming section of the thread forming tool. This provides for passively initial threading of the implant into the recess of the bone, and condensation of the bone at least at the apical portion of the implant 101, whereby improved stability can be obtained as well as a more controlled trajectory of the implant, as discussed above.

In some embodiments, a maximum diameter of a coronal portion of the bone tissue apposition surface is larger than a maximum diameter of a coronal portion of the thread forming section of the thread forming tool. This provides for condensation of the bone at least at the coronal portion of the implant 101, whereby improved stability can be obtained as well as a more controlled trajectory.

FIGS. 1a-1d illustrate certain embodiments of a procedure for providing a threading in bone in a procedure for guided surgery. The embodiments described below can be combined with the embodiments described above. The threading may comprise one or several threads 3a depending on the type of implant 1 being installed, such as an implant having a single or multiple lead thread. In the illustrated example, the bone 2 is a jawbone.

The guide sleeve 5 may be provided in the surgical template 6 as a separate or integrated component. Hence, the guide sleeve 5 may be integrated into or form part of the surgical template 6. In some embodiments, the guide sleeve is a metallic cylindrical sleeve which has been fixed to the surgical template 6, e.g. using an adhesive. In other embodiments, the guide sleeve 5 is detachable and can be inserted into a recess formed in the surgical template 6. The guide sleeve 5 has a guide surface 10 and a reference surface 11. The guide surface provides guidance to the drill 4a, 4b, 4c and/or the thread forming tool 7. Guiding in this context for certain embodiments is controlling the trajectory of the tool that is guided, such as in angular, vertical, lateral, and/or centering directions. The reference surface 11 can be used as the reference from which one or several depths or vertical directions are controlled. In the illustrated embodiment, a coronal end surface of the guide sleeve 5 serves as the reference surface. For example, the reference surface 11 has a fixed relationship relative to the planned position of the implant. Hence, by knowing the type and length of the implant 1, the depth of the recess 3 can be calculated, the correct depth drilled, and thread 3a provided at appropriate depth. The depth of any of the tooling can be controlled by markings on the tooling, such as visual or mechanical markings. A visual marking is for example a circumferential band indicating the distance to the tip of the tooling. A mechanical marking is for example a stop flange provided for abutment against the reference surface 11. The design of the guide sleeve 5 and the surgical template 6 as such is known from the NobelGuide™ planning and treatment concept mentioned above.

The thread forming tool 7 has a thread forming section 12 for forming at least one thread in bone. Also, the thread forming tool 7 comprises the guide section 8 for guidance by the guide surface 10 of the guide sleeve 5. The thread forming section 12 comprises an apical portion 13, and a coronal portion 14. The exact delimitation of the apical portion 13 and the coronal portion 14 may depend on the length of the entire thread forming section 12, which in turn may depend on the length and/or type of implant to be installed. However, in certain embodiments, a maximum diameter of the apical portion 13 of the thread forming section 12 is smaller than or equal to a maximum diameter of a cutting edge 15a, 15b, 15c of the drill 4a, 4b, 4c. When drilling the recess 3, the maximum diameter of the recess 3 will in certain embodiments correspond to the maximum diameter of the cutting edge 15a, 15b, 15c of the drill 4a, 4b, 4c. Hence, since the maximum diameter of the apical portion 13 of the thread forming section 12 is smaller than or equal to the maximum diameter of the cutting edge 15a, 15b, 15c of the drill 4a, 4b, 4c, the apical portion of the thread forming section 12 will be received within the recess 3 without condensing the bone 2 in certain embodiments. How long the apical portion 13 is received depends on the exact configuration of the apical portion 13 and the recess 3. After a certain distance, the thread forming section 12 in certain embodiments starts contacting the bone because it has a larger diameter than the recess 3, whereby threads are formed in the bone 2. By entering the thread forming section 12 in the recess 3 before the thread 3a is formed, positional control, such as centering, lateral, vertical, and/or angular control, of the thread forming section 12, is provided for in certain embodiments.

In the illustrated example, the recess 3 is stepped with a plurality of substantially circular cylindrical portions interconnected by a plurality of tapered portions. In other embodiments, the recess 3 is substantially circular cylindrical, tapered, or a combination thereof, which may be formed by a correspondingly shaped drill 4a, 4b, 4c or plurality of drills.

Figure 1B:
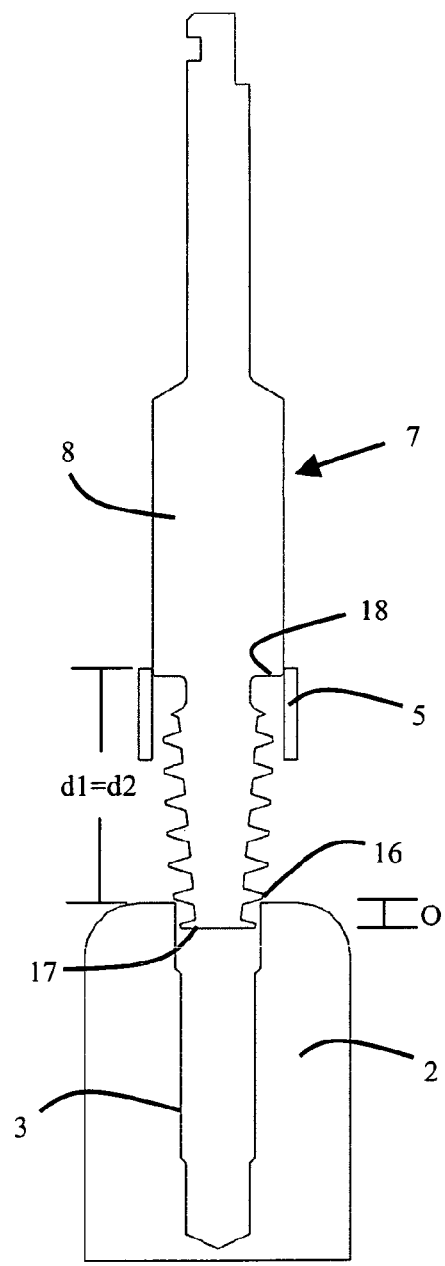

FIG. 1b illustrates an embodiment wherein a position 16 of the maximum diameter of the apical portion 13 of the thread forming section 12 is located offset O from an apical end 17 of the thread forming section 12. The position 16 is also located at a first distance d1 from an apical end 18 of the guide section 8. In the illustrated embodiment, the first distance d1 is substantially equal to a second distance d2, which is equal to the distance from the position 16 to a coronal end 19 of the guide surface 10 when the thread forming tool 7 is inserted into the guide sleeve 5. In the illustrated embodiment, the coronal end 19 of the guide surface 10 is located level with the reference surface 11. This embodiment provides for guidance by the guide sleeve 5 to the guide section 8 before the threaded section 12 engages the bone and starts generating the thread 3a in the bone 2. Hence, improved accuracy of the position of the thread 3a are provided for, such as improved angular, vertical, centering, and/or lateral control of the thread forming tool 7, and thus inherently improved accuracy of the position in space of the thread 3a in the bone 2.

In some embodiments, the offset O is at least 1 mm. In other embodiments, the offset is at least 2 mm or even at least 3 mm. The offset O may be in the range of 2-3 mm. The length of the offset O depends on the type of implant being installed and/or of the shape and dimension of the thread 3a that is to be provided in the bone 2. It may also depend on the length of the thread forming section 12.

In some embodiments, the apical end 17 of the thread forming section 12 is larger than a maximum diameter of an apical section 20a, 20b, 20c of the drill 4a, 4b, 4c. In embodiments other than for a substantially cylindrical drill, the apical section 20a, 20b, 20c of the drill may be smaller than a maximum diameter of a coronal section 21 of the drill 4a, 4b, 4c, such as for stepped drill or a tapered drill. This provides for providing threads in the recess along the entire length of the thread forming section 12. However, in other embodiments, the apical end 17 of the thread forming section 12 is smaller than or equal to a diameter of the apical section 20a, 20b, 20c of the drill 4a, 4b, 4c where the apical end 17 of the thread forming tool 7 is located when it is inserted to its final depth, which is illustrated in FIG. 1c. This provides for improved stability of the implant when it is inserted, e.g. if the implant 1 has a thread cutting tip which provides threads while it is inserted to its full depth. Yet, the thread 3a provided in the coronal portion of the recess 3 controls the position of the implant 1.

In certain embodiments, a diameter of the guide section 8 of the thread forming tool 7 is slightly smaller than a diameter of the guide surface of the guide sleeve, such as approximately 10-200 µm, for example 30-100 µm. This provides for the control of the trajectory of the thread forming tool 7, as discussed above.

The apical portion 13 of the thread forming section 12 may at least partially taper outwardly from the apical end 12 towards the coronal end of the thread forming section. In the embodiments illustrated in FIGS. 1a-1c, the entire thread forming section is tapering outwardly from its apical end to its coronal end. Here, both a tip 21 and a root 22 of a thread of the thread forming section 12 when viewed in cross-section tapers, i.e. the thread gradually increases in diameter from the apical end to the coronal end. In some embodiments, the gradual increase can be interrupted and instead a section with a generally cylindrical thread at the tip 21, the root 22, and/or in-between is provided.

Figure 2A:
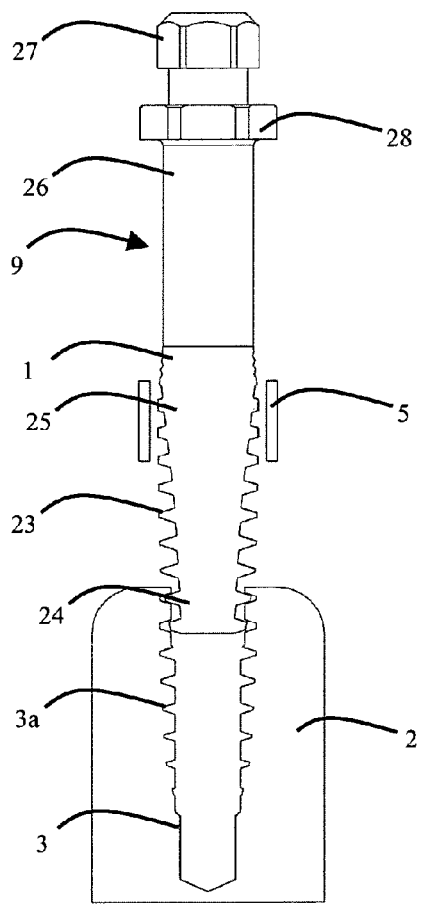
FIGS. 2a-2c are partially cross-sectional views of certain embodiments of an implant mount attached to an implant for placement into the recess in the bone at various stages of the placement procedure.
Figure 2B:
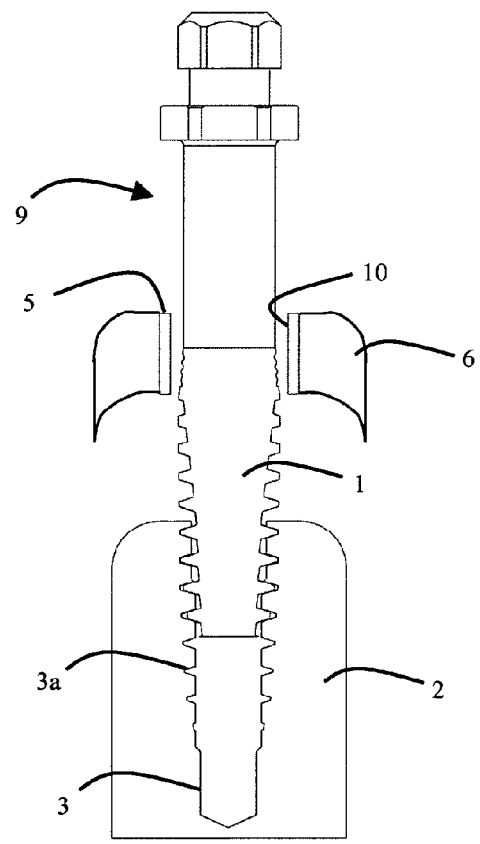
Figure 2C:
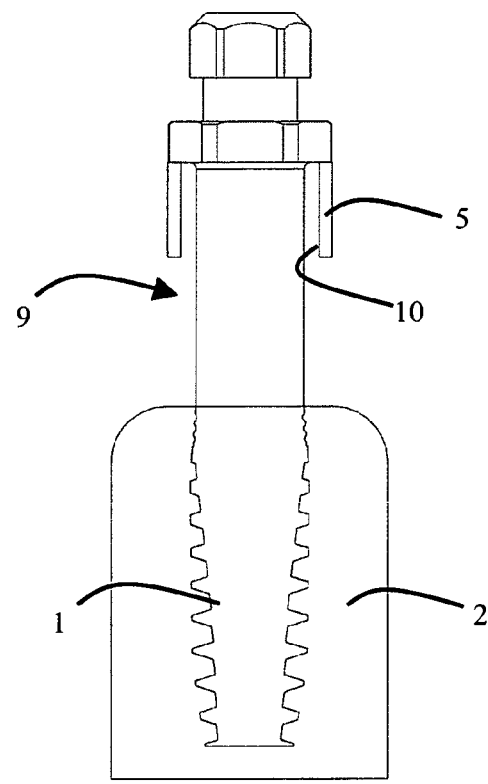

FIGS. 2a-2c illustrates the implant 1 and a procedure for placing the implant 1. The implant 1 has a bone tissue apposition surface 23, i.e. a surface that is in apposition to the bone 2 when the implant 1 is placed at its final position. For certain embodiments, a maximum diameter of at least an apical portion 24 of the bone tissue apposition surface 23 is smaller than or equal to a maximum diameter of the thread forming section 12 of the thread forming tool 7. This provides for passively threading the implant 1 into the thread 3a in the bone 2. Passively threading means in the context of certain embodiments that the implant can be inserted, such as by hand, to a certain depth substantially without condensing the bone. Hence there is a passive fit between the apical portion 24 of the bone tissue apposition surface 23 and the thread 3a in the bone 2. Hence, the thread 3 rather than the guide sleeve 5 may guide the implant, as will be discussed in more detail below. In some embodiments, it is enough if the implant can be screwed one or two full revolutions, depending on the type of thread, such as lead and/or pitch, how coarse the thread is, the number of leads, etc.

Figure 3A:
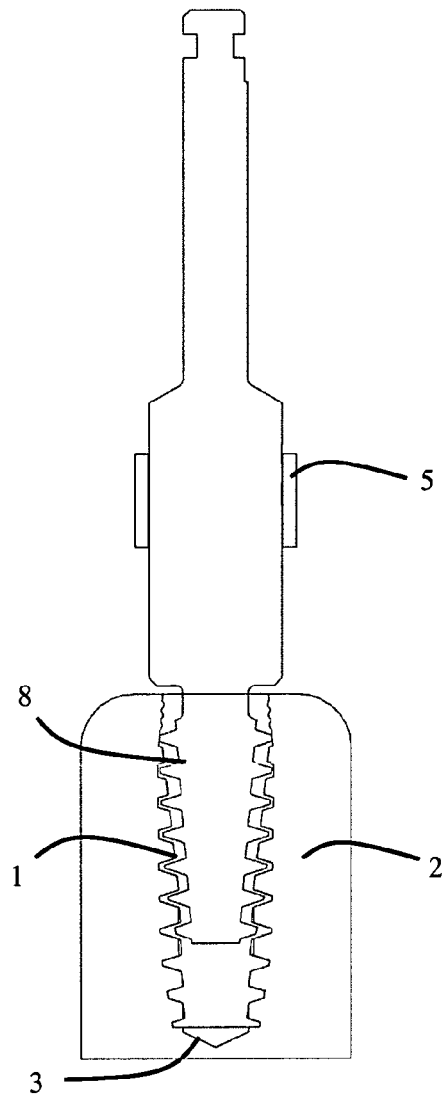
FIGS. 3a-3b are overlaid cross-sectional views of various sizes of certain embodiments of the implant and the tread forming tool.
Figure 3B:
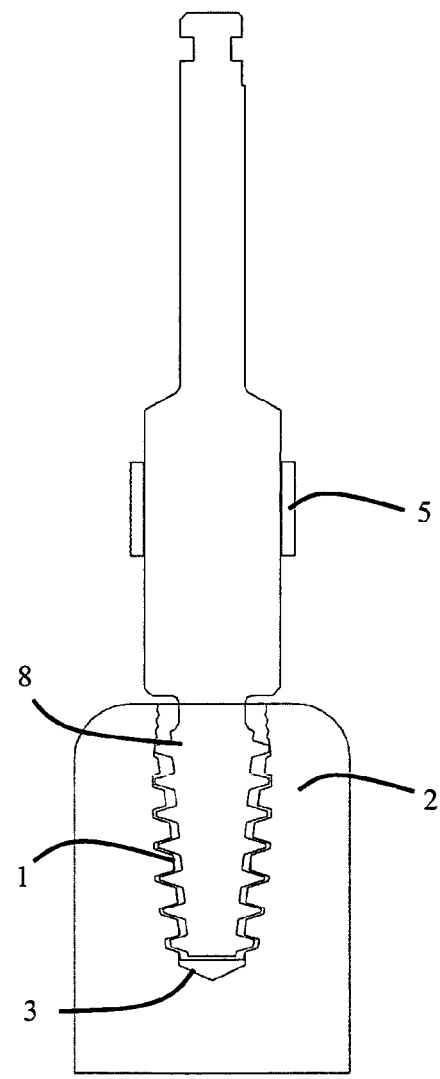

In some embodiments, a maximum diameter of the apical portion 24 of the bone tissue apposition surface 23 is larger than a maximum diameter of the apical portion 13 of the thread forming section 12 of the thread forming tool 7. This provides for improved stability of the implant, such as if the implant condenses the bone at least at the apical portion 24. This e.g. illustrated in FIG. 3b, wherein cross-sectional views of the thread forming tool 7 and the implant 1 are overlaid. In this embodiment, the length of the thread of the thread forming section 12 measured in the longitudinal direction of the thread forming tool 7 substantially corresponds to the length of the thread of the implant 1 measured in the longitudinal direction of the implant 1. Hence, the recess 3 is threaded substantially to its full depth. In other embodiments, such as illustrated in FIG. 3a, the length of the thread of the thread forming section 12 measured in the longitudinal direction of the thread forming tool 7 is shorter, such as at least 1 to 3 mm, than the length of the thread of the implant 1 measured in the longitudinal direction of the implant 1. Hence, the recess 3 is threaded only partially to its full depth. The latter embodiment provides for improved stability of the implant 1, such as if the implant condenses the bone and/or even cuts its own thread in the bone at the apical end 24.

In some embodiments, a maximum diameter of a coronal portion 25 of the bone tissue apposition surface 23 is larger than a maximum diameter of the coronal portion 14 of the thread forming section 12 of the thread forming tool 7. This provides for condensation of the bone also at the coronal region of the bone tissue apposition surface, such as to provide improved contact with cortical bone.

An embodiment of the implant mount 9 is illustrated in FIGS. 2a-2c. At one end, the implant mount 9 comprises a shank 26 with tool engaging head 27. The tool engaging head 27 has in this embodiment a hexagonal shape. Also, the implant mount has a depth indicator 28 indicating the appropriate depth of the implant. In this embodiment, the depth indicator is a tactile indicator, such as a flange, which provides tactile feedback to the user when the implant has reached its final or planner depth. The tactile feedback is e.g. provided when the flange abuts the reference surface 11 of the guide sleeve 5. Alternative, the depth indicator 28 may provide visual feedback, such as a visible marking, e.g. a circumferential band, in the shank 26.

As can be seen in the examples shown in FIGS. 2a-2c, clearance is provided between the guide surface 10 of the guide sleeve 5 and the shank 26. The guide surface 10 does not provide any guidance to the implant mount. Instead, guidance is provided by the thread 3a cut in the bone 2, such as lateral, centering, and/or angular guidance. This prevents that the implant mount 9 is jammed in the guide sleeve 5 and/or that the entire surgical template 6 is dislocated from its accurate position. Hence, improved positional accuracy is provided for in certain embodiments, not only for the implant 1 that is actually being installed, but also for any additional implants being installed using the same surgical template 6.

In certain embodiments, at least one of an apical section and a coronal section of the drill is substantially cylindrical, such as circular cylindrical, tapered, or cylindrical and taped.

Figures 4A, 4B, 4C:
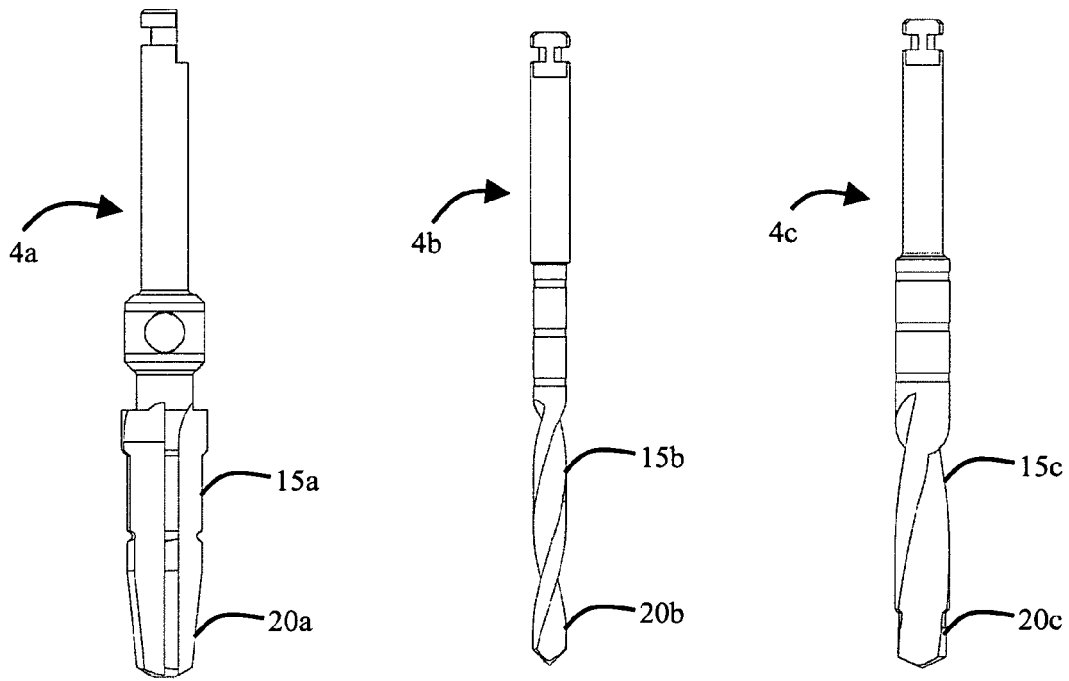
FIGS. 4a-4c are side views of certain embodiments of drills.

FIGS. 4a-4c illustrates various embodiments of drills 4a, 4b, 4c for forming the recess 3 in the bone 2. Each drill 4a, 4b, 4c has at least one cutting edge 15a, 15b, 15c for cutting the recess 3a in the bone 2.

The drill 4a of the embodiment of FIG. 4a is at least partially tapered, i.e. its cutting edge 15a forms substantially a circular cylinder at a coronal portion of the edge and tapered cone or truncated cone at an apical portion of the cutting edge 15a. The tapered portion may be in the range of 20-80% of the total length of the cutting edge 15a measured in the axial direction of the drill 4a.

The drill 4b of the embodiment of FIG. 4b is substantially cylindrical. The cutting edge 15b of the cylindrical drill 4b is helical with a constant outer diameter.

The drill 4c of the embodiment of FIG. 4c is a stepped drill, wherein the outer diameter of the cutting edge 15c varies along the axial direction of the drill 4c. The edge as such is helical. The diameter of the cutting edge relative the longitudinal central axis of the drill 4c at the apical portion 20c is smaller than the diameter of the coronal portion of the drill.

Figure 4D:
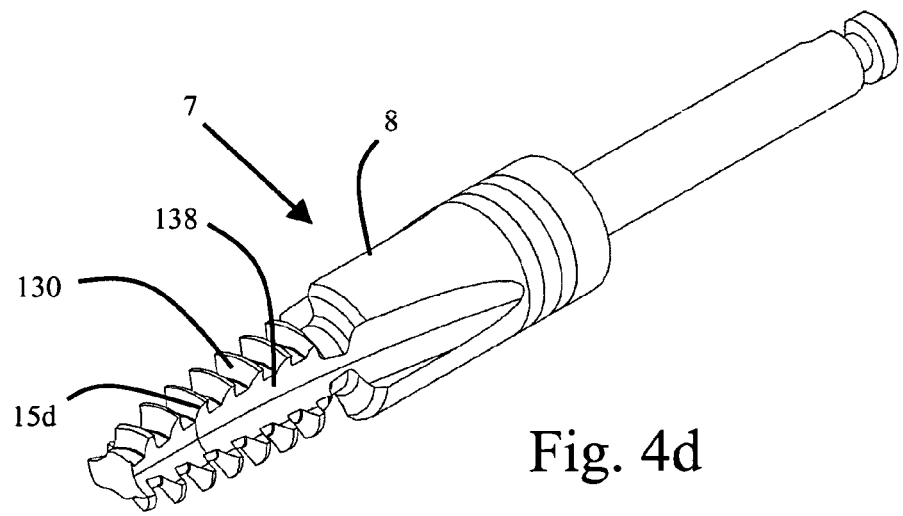
FIG. 4d is a perspective view of certain embodiments of the thread forming tool.

FIG. 4d illustrates an embodiment of the thread forming tool 7. The thread 130 of the thread forming tool 7 is helical and interrupted by at least one cutting surface 15d on each revolution of the thread 130 around the perimeter of the thread forming section. A recess 138 is formed in the thread 130 starting at the tip of the thread forming section and ends on the guiding section.

Components according to some embodiments provide for passively inserting an implant in bone at least initially when it is placed. Passively threading means in the context of certain embodiments that the implant can be inserted, such as by hand, to a certain depth without condensing the bone. The implant may contact the bone, but substantially not condense. Hence, a passive fit between the implant and the bone is provided. This provides for the implant more closely following an anticipated trajectory, i.e. is guided by the bone, and/or a more uniform condensation of the bone 2 when the implant 1 is placed.

The length of the implant 101 from its apical to its coronal end may be in the range of 6-20 mm, such as 8-18 mm. The maximum diameter of the thread of the implant may be in the range of 1.8-5.5 mm, such as 2.5-5.0 mm. As discussed above, the length and diameter of the thread forming section of the thread forming tool may be equivalent or slightly less than the dimensions of the implant 1. In some situations, the length and diameter of the thread forming section of the thread forming tool may be slightly larger than the dimensions of the implant.

An embodiment of a method of placing an implant in a threaded recess in bone, comprises drilling a recess in bone, forming a thread in the recess having a shape which at least partially corresponds to a shape of a thread of an implant, and inserting said implant in said threaded recess.

An embodiment of a method for forming the thread 3a in the bone 2, comprises positioning a surgical template having a guide sleeve with a guide surface at a surgical site, inserting a drill through the guide sleeve, drilling a recess in the bone while the drill is guided by the guide sleeve, inserting a thread forming tool into the guide sleeve, guiding a guide section of the thread forming tool with the guide surface of the guide sleeve before a thread forming section of the thread forming tool starts forming a thread in the recess, and forming a thread in the bone while the guide section of the thread forming tool is guided by the guide surface.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

What is claimed is:

1. A combination of a thread forming tool and an implant for placing the implant in a jawbone or for oral or craniomaxillofacial implant placement, the combination comprising:

the thread forming tool comprising, at an apical end of the tool, a thread forming section with a helical thread having at least one cutting surface for cutting a thread in bone, the helical thread of the thread forming section comprising a plurality of crests and roots;

the implant comprising a bone apposition surface having at least one helical thread for position at least partially in the thread of the bone, the helical thread of the bone apposition surface comprising a plurality of crests and roots, wherein a longitudinal cross-sectional shape of at least a portion of the helical thread of the thread forming section substantially corresponds to a longitudinal cross-sectional shape of at least a portion of the helical thread of the implant;

a drill; and a guide sleeve for a surgical template, wherein a dimension of said cross-sectional shape of the helical thread of the thread forming section is smaller than a corresponding dimension of said cross-sectional shape of the helical thread of the implant, wherein the crests or the roots of the thread forming section are tapering outwardly relative to the central longitudinal axis of the tool from an apical end of the thread forming section towards a coronal end for substantially all of the thread forming section, and the crests or the roots of the bone apposition surface of the implant are tapering outwardly relative to the central longitudinal axis of the implant from an apical end of the implant towards a coronal end for substantially all of the bone apposition surface of the implant, wherein a maximum diameter of an apical portion at one of the plurality of crests of the bone apposition surface is larger than a maximum diameter of an apical portion at one of the plurality of crests of the thread forming section of the thread forming tool, and smaller than a coronal portion of the thread forming section of the thread forming tool, wherein the guide sleeve has a guide surface on an inner surface of the guide sleeve for guiding the thread forming tool, wherein the drill has at least one cutting edge on an apical section and a coronal section, wherein the thread forming tool has a guide section for guidance by the guide surface of the guide sleeve, and wherein the maximum diameter of the apical portion of the thread forming section is smaller than or equal to a maximum diameter of the cutting edge of the drill.

2. The combination according to claim 1, wherein said dimension of the thread forming section is the radius from the central longitudinal axis of the thread forming tool to an external surface of a crest of its thread, and said dimension of the thread of the implant is the radius from the central longitudinal axis of the implant to an external surface of a crest of its thread.

3. The combination according to claim 1, wherein said dimension of the thread forming section is the radius from the central longitudinal axis of the thread forming tool to an external surface of a root of its thread, and said dimension of the thread of the implant is the radius from the central longitudinal axis of the implant to an external surface of a root of its thread.

4. The combination according to claim 1, wherein a pitch of the helical thread of the thread forming section is substantially equal to a pitch of the helical thread of the implant.

5. The combination according to claim 1, wherein a maximum diameter of at least the apical portion of the bone apposition surface is smaller than or equal to a maximum diameter of the thread forming section of the thread forming tool.

6. The combination according to claim 1, wherein a maximum diameter of a coronal portion of the bone apposition surface is larger than a maximum diameter of the coronal portion of the thread forming section of the thread forming tool.

7. The combination according to claim 1, wherein a position of the maximum diameter of the apical portion of the thread forming section is located offset from the apical end of the thread forming section and at a first distance from an apical end of the guide section, wherein the combination is configured to have said first distance being substantially equal to a second distance from said position to a coronal end of the guide surface when the thread forming tool is partially inserted into the guide sleeve such that the guide sleeve provides guidance before the thread forming section engages the bone.

8. The combination according to claim 7, wherein the offset is at least about 1 mm.

9. The combination according to claim 1, wherein the apical end of the thread forming section is larger than a maximum diameter of the apical section of the drill, the apical section of the drill smaller than a maximum diameter of the coronal section of the drill.

10. The combination according to claim 8, wherein the offset is at least about 2 mm.

11. The combination according to claim 10, wherein the offset is in a range of about 2 mm to about 3 mm.

12. The combination according to claim 1, wherein the level of taper as indicated by straight lines interconnecting a number of the crests or a number of the roots of the bone apposition surface relative to the central longitudinal axis of the implant at the coronal end of the implant compared to the apical end of the implant is less for both the crests and the roots of the bone apposition surface.

13. A method of placing an implant in a threaded recess in bone, the method comprising:
providing the combination according to claim 1;
drilling a recess in the bone with the drill;
forming with the thread forming tool, a thread in the recess having a shape which at least partially corresponds to a shape of the helical thread of the implant; and
inserting said implant in said threaded recess.

* * * * *